(12) United States Patent
DiLoreto et al.

(10) Patent No.: US 11,654,026 B2
(45) Date of Patent: *May 23, 2023

(54) PENILE IMPLANT

(71) Applicant: Boston Scientific Scimed, Inc., Maple Grove, MN (US)

(72) Inventors: Mark Edward DiLoreto, Chaska, MN (US); Karl Alan Jagger, Deephaven, MN (US); Thomas Skoog, Elk River, MN (US); Robert J. Berkenes, Buffalo, MN (US); Alex Alden Peterson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 324 days.

This patent is subject to a terminal disclaimer.

(21) Appl. No.: 16/844,491

(22) Filed: Apr. 9, 2020

(65) Prior Publication Data

US 2020/0229929 A1 Jul. 23, 2020

Related U.S. Application Data

(63) Continuation of application No. 16/027,704, filed on Jul. 5, 2018, now Pat. No. 10,653,525.

(60) Provisional application No. 62/529,708, filed on Jul. 7, 2017.

(51) Int. Cl.
*A61F 2/26* (2006.01)
*A61F 5/41* (2006.01)
*A61F 2/48* (2006.01)

(52) U.S. Cl.
CPC .............. *A61F 2/26* (2013.01); *A61F 5/41* (2013.01); *A61F 2/48* (2021.08); *A61F 2005/411* (2013.01); *A61F 2005/415* (2013.01); *A61F 2250/0003* (2013.01)

(58) Field of Classification Search
CPC ..................................... A61F 2/26; A61F 5/41
See application file for complete search history.

(56) References Cited

U.S. PATENT DOCUMENTS

| | | | |
|---|---|---|---|
| 4,517,967 A | 5/1985 | Timm et al. | |
| 4,522,198 A | 6/1985 | Timm et al. | |
| 4,541,420 A | 9/1985 | Timm et al. | |
| 4,545,081 A | 10/1985 | Nestor et al. | |
| 4,619,251 A | 10/1986 | Helms et al. | |
| 4,666,428 A | 5/1987 | Mattioli et al. | |
| 4,807,608 A | 2/1989 | Levius | |
| 10,653,525 B2 * | 5/2020 | DiLoreto | A61F 2/26 |

FOREIGN PATENT DOCUMENTS

| | | |
|---|---|---|
| CN | 1416329 A | 5/2003 |
| CN | 102686186 A | 9/2012 |
| EP | 0182574 A1 | 5/1986 |
| EP | 0301741 A1 | 2/1989 |
| EP | 0320203 A1 | 6/1989 |
| WO | 8404035 A1 | 10/1984 |

* cited by examiner

*Primary Examiner* — John P Lacyk
(74) *Attorney, Agent, or Firm* — Brake Hughes Bellermann LLP

(57) ABSTRACT

According to an aspect, an implant includes a sheath defining a lumen, a cable member disposed within the lumen defined by the sheath, and a tensioner. The tensioner is configured to engage the cable to apply tension to the sheath.

19 Claims, 4 Drawing Sheets

PENILE IMPLANT

CROSS-REFERENCE TO RELATED APPLICATIONS

This application is a continuation of, and claims priority to, U.S. patent application Ser. No. 16/027,704, filed on Jul. 5, 2018, entitled "PENILE IMPLANT", which claims priority to U.S. Patent Application No. 62/529,708, filed on Jul. 7, 2017, entitled "PENILE IMPLANT", and NL Patent Application No. 2019790, filed on Oct. 24, 2017, the disclosures of which are incorporated by reference herein in their entireties.

TECHNICAL FIELD

This disclosure relates generally to bodily implants and more specifically to bodily implants, such as penile prostheses, that may be placed in multiple configurations.

BACKGROUND

One treatment for male erectile dysfunction is the implantation of a penile prosthesis that may be placed in multiple configurations. For example, some existing penile prostheses may be implanted in or near the penis of the patient and may be disposed in a first configuration to place the penis in a flaccid-like state and may be disposed in a second configuration to place the penis in an erect-like state. Some existing implants include complex activation mechanisms to change the configurations of the implants and may require a large amount of effort to change or convert the implant from one configuration to another configuration.

Accordingly, it would be useful to provide a bodily implant, such as a penile prosthesis that may efficiently be moved from one configuration to another configuration.

SUMMARY

According to an aspect, an implant includes a sheath defining a lumen, a cable member disposed within the lumen defined by the sheath, and a tensioner. The tensioner is configured to engage the cable to apply tension to the sheath.

In an embodiment, the sheath is configured to be placed in a first configuration and a second configuration. For example, in one embodiment, the sheath is configured to be placed in a linear configuration and a curved configuration.

In an embodiment, the cable member has a first end portion and second end portion, the first end portion of the cable member being operatively coupled within the lumen defined by the sheath, the second end portion of the cable member being operatively coupled within the lumen defined by the sheath. In another embodiment, the cable member has a first end portion and second end portion, the first end portion of the cable member being operatively coupled at a first end portion of the lumen defined by the sheath, the second end portion of the cable member being operatively coupled at a second end portion of the lumen defined by the sheath.

In an embodiment, the tensioner includes a bias member. For example, in an embodiment, the tensioner includes a spring member.

In an embodiment, the tensioner includes a release member, the release member being configured to extend through an opening defined by the sheath. In another embodiment, the tensioner includes a release member, the release member being configured to accessed through an opening defined by the sheath.

In an embodiment, the tensioner includes a release member, the release member being movable with respect to the sheath. In an embodiment, the tensioner includes a release member and a plunger member, the release member having an engagement portion, the engagement portion being configured to engage the plunger member to help retain the sheath in a first configuration. In another embodiment, the tensioner includes a release member and a plunger member, the release member being configured to engage the plunger member to help retain the sheath in a linear configuration.

In an embodiment, the sheath defines a plurality of slots. For example, in one embodiment, the sheath defines a plurality of non-linear slots. In an embodiment, the sheath defines a pattern of openings.

According to another aspect, a penile implant includes a sheath having a sidewall defining a lumen extending along a longitudinal axis of the sheath, the sidewall defining a plurality of slots; a cable member disposed within the lumen of the sheath; and a tensioner configured to engage the cable to apply tension to the sheath.

In an embodiment, the slots are non-linear slots.

In an embodiment, the sheath is configured to be placed in a linear configuration and a curved configuration.

According to an aspect a penile implant includes a sheath having a sidewall, the sidewall defining a plurality of slots; a cable member coupled to the sheath; and a tensioner configured to engage the cable to apply tension to the sheath.

In an embodiment, the sheath is configured to be placed in a linear configuration and a curved configuration.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to medical devices such as penile prostheses or other bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The terms proximal and distal described in relation to various devices, apparatuses, and components as discussed in the subsequent text of the present disclosure are referred with a point of reference. The point of reference, as used in this description, is a perspective of a person who implants the device such as the penile prosthesis. The person may be a surgeon, a physician, a nurse, a doctor, a technician, and the like who may perform the implantation procedure. The term proximal refers to an area or portion that is closer or closest to the person during the implantation procedure. The term distal refers to an area or portion that is farther or farthest from the person.

The embodiments discussed herein may improve the performance of a penile prosthesis. For example, the penile prosthesis may have improved usability. Specifically, the penile prosthesis may require a small amount of effort to convert the implant from a first configuration to a second configuration. Additionally, the penile prosthesis may require less effort to implant the device into the body of a patient.

Figure 1:
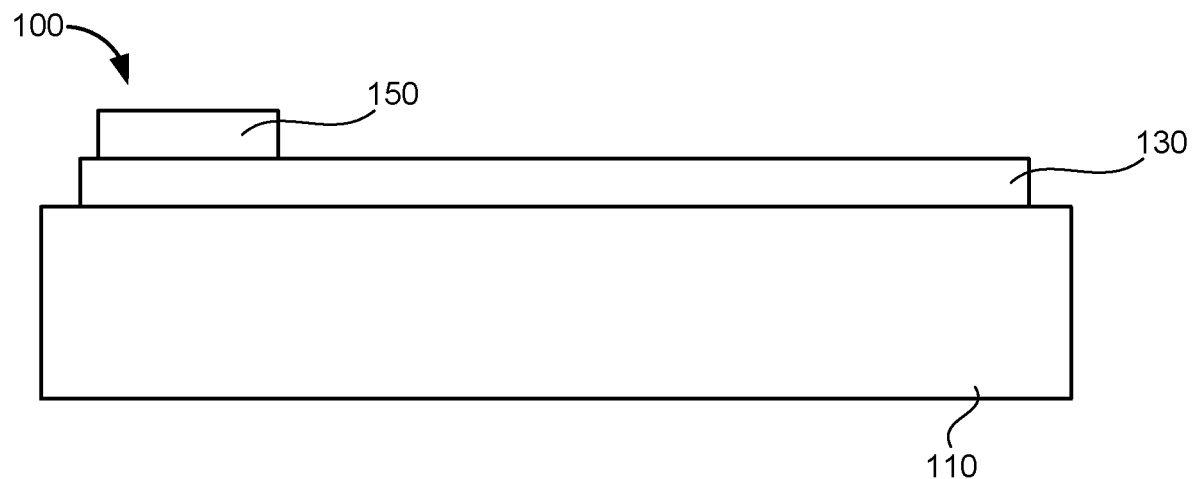
FIG. 1 schematically illustrates a penile prosthesis according to an embodiment.

FIG. 1 schematically illustrates an implant 100 according to an aspect. The implant 100 includes a sheath or sheath member 110, a cable or cable member 130, and a tensioner 150. The implant 100 may be disposed or placed within a body of a patient or user. For example, in some embodiment, the implant 100 may be a penile implant and the implant 100 may be placed within a penis of a patient. Specifically, in some embodiments, the implant 100 may be implanted within the corpus cavernosum of the patient. In other embodiments, the implant may be placed in other locations within the body of the patient.

In some embodiments, more than one implant 100 may be placed within the body of the patient. For example, in some embodiments, two implants 100 may be placed within the body of the patient. Specifically, in some embodiments, two implants 100 may be placed within a penis of the patient. The implants may be placed within the penis of the patient in substantially parallel or side-by-side arraignment. In other embodiments, only one implant 100 is disposed or implanted within the body of the patient.

As will be described in more detail below, the implant 100 may be placed in a first configuration and a second configuration different than the first configuration. For example, in some embodiments, the implant 100 may be able to be placed in a straight or linear configuration and in a curved or non-linear configuration. Accordingly, in some embodiments, the implant 100 may be placed within a penis of the patient and the patient may selectively place the implant in (1) a straight or linear configuration to achieve or simulate an erect penis or (2) a curved or non-linear configuration to achieve or simulate a flaccid penis.

The sheath or sheath member 110 is an elongate member and is configured to be placed in a first configuration and second configuration different than the first configuration. For example, in some embodiments, the sheath 110 may be able to be placed in a straight or linear configuration and in a curved or non-linear configuration. In some embodiments, the sheath 110 or a sidewall of the sheath 110 defines or includes a slot or an opening or a plurality of slots or openings. In some embodiments, the sheath 110 includes or defines a pattern of slots or openings. The slots or openings may be configured to allow or facilitate the placement of the sheath 110 in the different configurations. In some embodiments, the sheath 110 defines slots or openings along only a portion of the length of the sheath.

In some embodiments, the sheath 110 defines a lumen. The lumen may extend from one end portion of the sheath 110 to an opposite end portion of the sheath 110. The lumen may house or receive other components of the implant 100. In other embodiments, the sheath 110 does not include or define a lumen.

The cable or cable member 130 is coupled to sheath 110 and is configured to selectively apply tension to the sheath 110. In some embodiments, the cable or cable member 130 may apply tension to the sheath 110 to place the sheath in its first, straight, or linear configuration. As discussed in more detail below, the tension may be removed from the sheath 110 to place the sheath in its second, curved, or non-linear configuration.

In some embodiments, the cable 130 is coupled to the sheath 110 at a first end portion of the sheath and at a second end portion of the sheath 110. In other embodiments, the cable 130 is coupled to other portions of the sheath 110. For example, in some embodiments, the cable 130 is coupled to the sheath 110 at other locations along the length of the sheath 110.

In some embodiments, the cable 130 is of a fixed length and is non-extendable. In other words, the cable 130 is configured such that does not stretch or has very little capacity to stretch or lengthen. Accordingly, the cable 130 is also able to apply tension to the sheath 110. In some embodiments, the cable 130 is formed of or from a material that has little capacity to stretch.

The tensioner 150 is operatively coupled to the sheath 110 and to the cable 130. The tensioner 150 is configured to engage the cable 130 such that tension may be selectively applied to the sheath 110. In some embodiments, the tensioner 150 includes a release member. The release member is configured to help retain tension on sheath 110 and may be actuated to selectively release the tension applied to the sheath 110.

Figure 2:
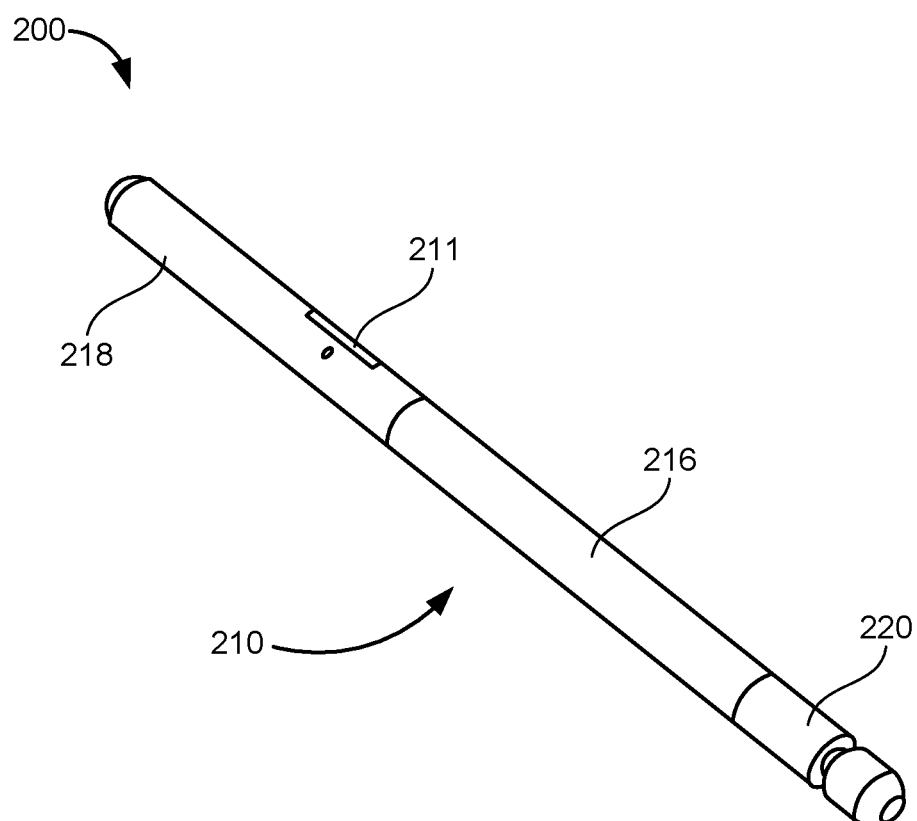
FIG. 2 is a perspective view of a penile prosthesis according to an embodiment.
Figure 3:
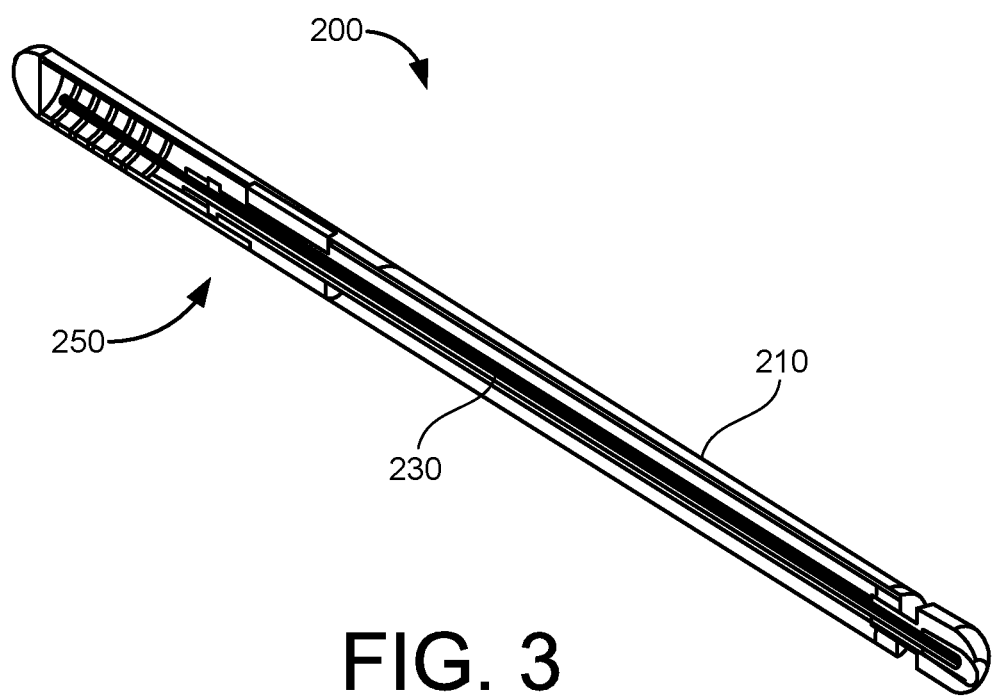
FIG. 3 is a cross-sectional view of the penile prosthesis of FIG. 2.
Figure 4:
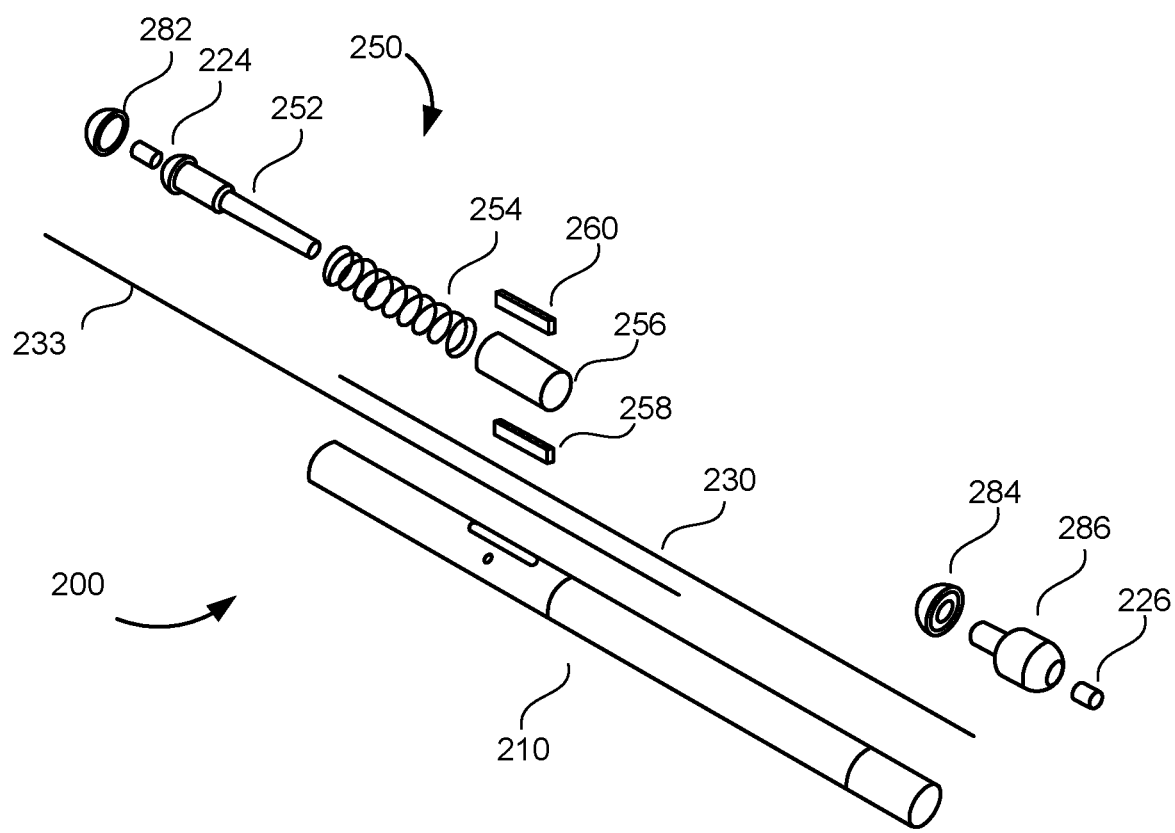
FIG. 4 is an exploded view of the penile prosthesis of FIG. 2.
Figure 5:
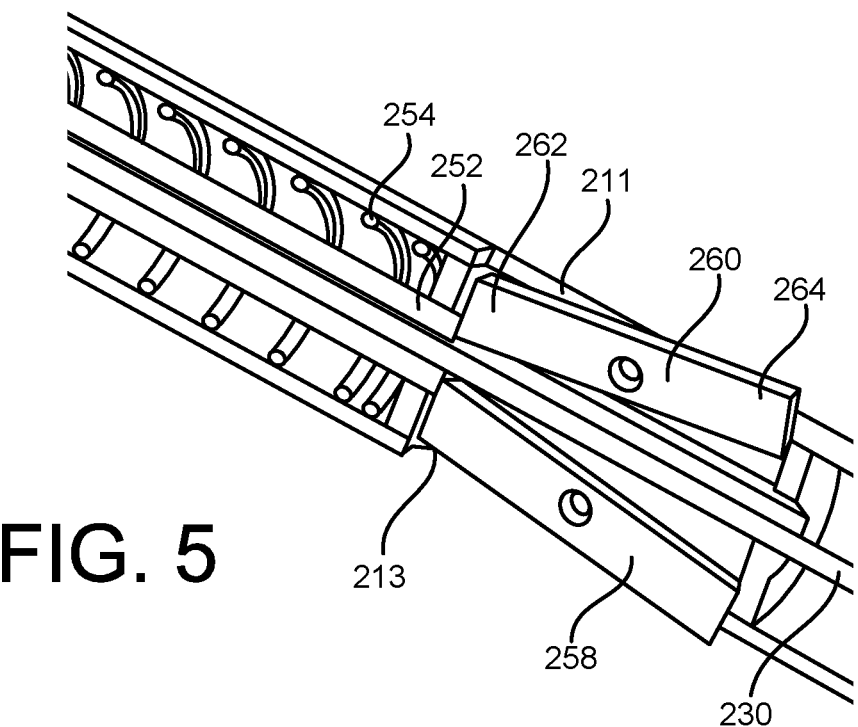
FIG. 5 is a cross-sectional view of a portion of the penile prosthesis of FIG. 2 in a first configuration.
Figure 6:
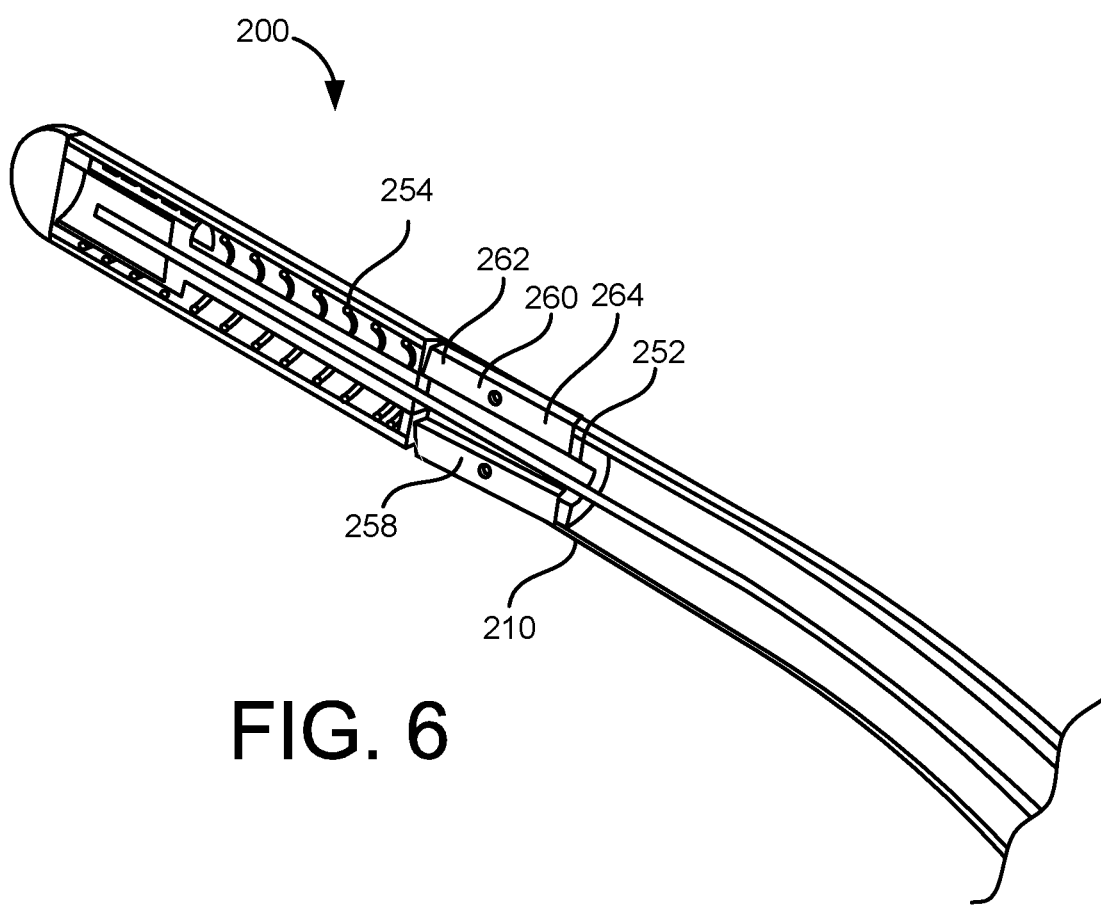
FIG. 6 is a cross-sectional view of a portion of the penile prosthesis of FIG. 2 is a second configuration.
Figure 7:
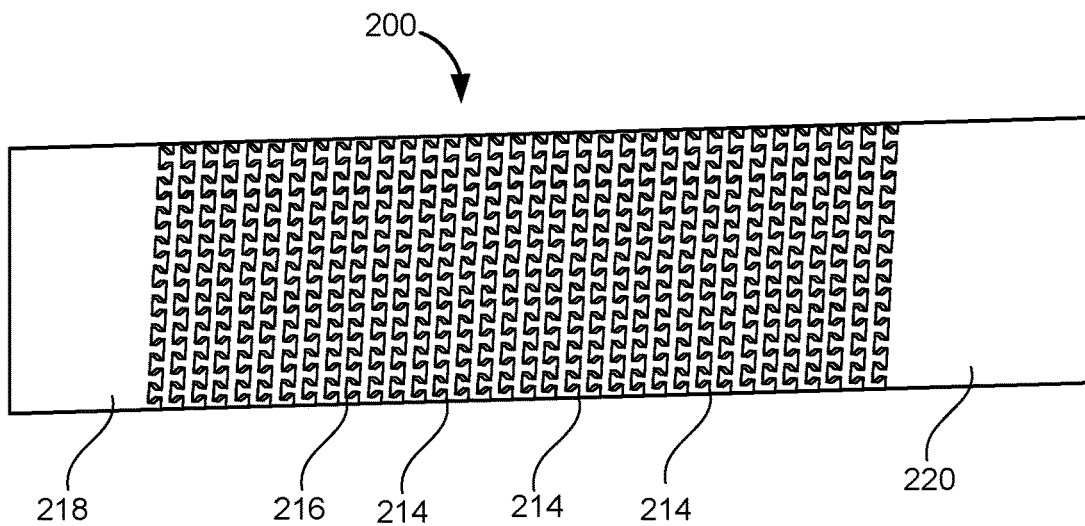
FIG. 7 is a top view of a portion of a sheath of the penile prosthesis of FIG. 2.
Figure 8:
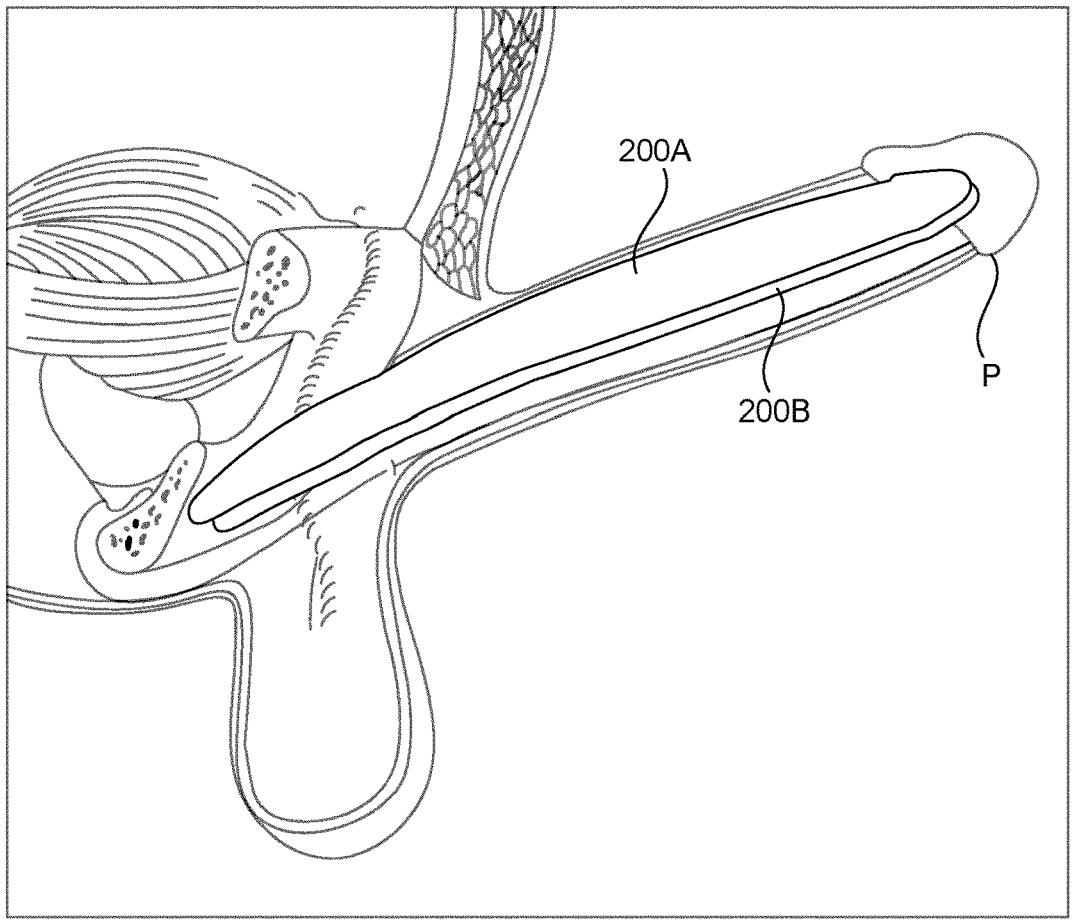
FIG. 8 is a schematic illustration of a penile prosthesis disposed within a body of a patient.

FIGS. 2-8 illustrate an implant 200 according to an aspect. FIG. 2 is a perspective view of the implant 200. FIG. 3 is a cross-sectional view of the implant 200. FIG. 4 is an exploded view of the implant 200. FIG. 5 is a cross-sectional view of a portion of the implant 200 while the implant 200 is in a first configuration. FIG. 6 is a cross-sectional view of a portion of the implant 200 while the implant 200 is in a second configuration. FIG. 7 is a side view of a sheath 210 of the implant 200. FIG. 8 schematically illustrates the implant 200 disposed within a body of a patient.

The implant 200 includes a sheath or sheath member 210, a cable or cable member 230, and a tensioner 250. The implant 200 may be disposed or placed within a body of a patient or user. For example, in some embodiment, the implant 200 may be a penile implant and the implant 200 may be placed within a penis of a patient. Specifically, in some embodiments, the implant 200 may be implanted within the corpus cavernosum of the patient. In other embodiments, the implant 200 may be placed in other locations within the body of the patient.

In some embodiments, more than one implant 200 may be placed within the body of the patient. For example, in some embodiments, two implants 200 may be placed within the body of the patient. Specifically, in some embodiments, two implants 200 may be placed within a penis of the patient. The implants may be placed within the penis of the patient in a substantially parallel or a side-by-side arraignment. In other embodiments, only one implant 200 is disposed or implanted within the body of the patient.

As will be described in more detail below, the implant 200 may be placed in a first configuration and a second configuration different than the first configuration. For example, in some embodiments, the implant 200 may be able to be placed in a straight or linear configuration and in a curved or non-linear configuration. Accordingly, in some embodiments, the implant 200 may be placed within a penis of the patient and the patient may selectively place the implant 200 in (1) a straight or linear configuration to achieve or simulate an erect penis or (2) a curved or non-linear configuration to achieve or simulate a flaccid penis.

The sheath or sheath member 210 is an elongate member and is configured to be placed in a first configuration and second configuration different than the first configuration. For example, in some embodiments, the sheath 210 may be able to be placed in a straight or linear configuration and in a curved or non-linear configuration.

The sheath 210 includes a sidewall 212. As best illustrated in FIG. 7, in the illustrated embodiment, the sidewall 212 of the sheath 210 defines or includes a series or a plurality of slots or openings 214. The slots or openings 214 extend through the sidewall 212. Specifically, in the illustrated embodiment, the sidewall 212 of the sheath 210 includes or defines a pattern of slots or openings. The slots or openings 214 allow or facilitate the placement of the sheath 210 in the different configurations. Specifically, the slots or openings 214 allow the sheath 210 to be flexible at the locations of the slots or openings 214. Accordingly, the sheath 210 may bend or flex at the location of the slots or openings. In the illustrated embodiment, the slots or openings 214 are non-linear. In other embodiments, the slots or openings 214 are linear. In some embodiments, the adjacent portions of the sidewall 212 that define the slots or openings 214 are configured to engage each other and lock into place. In some embodiments, such engagement may increase the columnar strength of the sheath 210 when the sheath is in its straight or linear configuration.

In the illustrated embodiment, the sidewall 212 of the sheath 110 defines slots or openings along a middle portion 216 of the sheath 110. The sidewall 212 is solid (or does not define slots or openings) at the end portions 218 and 220 of the sheath. In other embodiments, the openings or slots may be present along more or less of the sheath.

In the illustrated embodiment, the sheath 210 defines a lumen 222. The lumen 222 extends from the first end portion 218 of the sheath 210 to the second end portion 220 of the sheath 210. As discussed below, the lumen 222 is configured to house or receive other components of the implant 200. In other embodiments, the sheath 210 does not include or define a lumen.

The sheath 210 may be formed of any biocompatible material. In some embodiments, the sheath 210 is formed of a rigid material. For example, in some embodiments, the sheath 210 is formed of a polymer material. In other embodiments, the sheath 210 is formed of a metal material.

The cable or cable member 230 is coupled to sheath 210 and is configured to selectively apply tension to the sheath 210. In some embodiments, the cable or cable member 230 may apply tension to the sheath 210 to place the sheath in its first, straight, or linear configuration. As discussed in more detail below, the tension may be removed from the sheath 210 to place the sheath in its second, curved, or non-linear configuration.

In the illustrated embodiment, the cable 230 is disposed within the lumen 222 defined by the sheath 210. The cable 230 is coupled to the sheath 210 at the first end portion 218 of the sheath 210 and at the second end portion 220 of the sheath 210. Specifically, in the illustrated embodiment, the cable 230 is coupled to the first end portion 218 of the sheath 210 via a crimp member 224. The cable 230 is coupled to the second end portion 220 if the sheath 210 via a crimp member 226.

In the illustrated embodiment, the device includes a centering member 233. The centering member 233 may be configured to be disposed between the cable 230 and the sheath 210. The centering member 233 is configured to help retain the cable 230 in or along the center of the sheath 210. For example, in some embodiments, the centering member 233 is an elongate member that defines a lumen. In such embodiments, the cable 230 is disposed within the lumen of the centering member 233.

In other embodiments, the cable 230 is coupled to other portions of the sheath 210. For example, in some embodiments, the cable 230 is coupled to the sheath 210 at other locations along the length of the sheath 210.

The cable 230 is of a fixed length and is non-extendable. In other words, the cable 230 is configured such that does not stretch or has very little capacity to stretch or lengthen. Accordingly, the cable 230 is able to apply tension to the sheath 210. In some embodiments, the cable 230 is formed of or from a material that has little capacity to stretch.

The tensioner 250 is operatively coupled to the sheath 210 and to the cable 230. The tensioner 250 is configured to engage the cable 230 such that tension may be selectively applied to the sheath 210.

In the illustrated embodiment, the tensioner 250 includes a plunger member 252, a bias member 254, a plunger guide 256, a first release member 258, and a second release member 260. In the illustrated embodiment, the plunger member 253, the bias member 254, and the plunger guide 256 are disposed within the lumen 222 defined by the sheath 210. Additionally, in the illustrated embodiment, the cable 230 extends through the plunger member 252, the bias member 254, and the plunger guide 256.

In the illustrated embodiment, the bias member 254 is configured to provide a bias to the tensioner 250. Specifically, the bias member 254 is configured to provide a bias to the tensioner 250 such that the tension is removed from the sheath 210. Accordingly, the sheath 210 is biased to its curved or non-linear configuration. In the illustrated embodiment, the bias member 254 is a spring member. In other embodiments, the bias member 254 is a different type of bias member. In some embodiments, the cable 230 is configured to move or slide within the sheath 210 when moved from the tensioned position and the non-tensioned position. In some embodiments, the amount of movement is about 1 cm. In other embodiments, the cable 230 is configured to slide or move more with respect to the sheath 210.

In the illustrated embodiment, release members 258 and 260 are structurally and functionally similar. Accordingly, only release member 260 will be discussed in detail.

The release member 260 is configured to help retain tension on sheath 210 and may be actuated to selectively release the tension applied to the sheath 210. The release member 260 is moveable with respect to the sheath 210. In the illustrated embodiment, the release member 260 is pivotably movable with respect to the sheath 210. For example, the release member 260 may be pivotably coupled to the sheath 210 or may be pivotally coupled to the plunger guide 256 or to another portion of the tensioner 250.

The release member 260 includes an engagement portion 262. As best illustrated in FIG. 5, the engagement portion 262 is configured to contact a portion of the plunger member 252 to help retain the sheath 210 in its first, straight, or linear configuration. The release member 260 also includes an activation portion 264. The activation portion 264 may be used or moved with respect to the sheath 210 to pivot or rotate the release member 260. Movement or rotation of the release member 260 causes the engagement portion 262 to disengage the plunger member 252. The plunger member 252 will then be moved by the bias member 254 and the sheath 210 will assume its second, curved, or non-linear configuration.

In the illustrated embodiment, the sheath 210 defines a window or opening 211. In the illustrated embodiment, a portion of the release member 260 extends from the window or opening 211. Note that the release member 258 extends from another window or opening 213 defined by the sheath 210. Accordingly, a user may access the release member 260 to activate or apply pressure to the activation portion 264 of the release member 260. For example, in some embodiments, when the implant 200 is disposed within a body of the patient, the user may contact or active the release member 260 by pressing on skin or bodily tissue. In some embodiments, the release member 260 is accessible by a user through the window or opening 211. For example, in some embodiments, the release member 260 does not extent through the window or opening 211.

The implant also includes an end cap 282 coupled to the first end portion 218 of the sheath 210. Similarly, the implant 200 also includes a front tip base 284 and a front tip 286 coupled to the second end portion 220 of the sheath 210.

In some embodiments, the implant 200 may include a sleeve or cover that is configured to extend about an outside surface of the sheath 210. In some embodiments, the sleeve or cover may cover the entire outer surface of the sheath 210. In other embodiments, the sleeve or cover may cover only a portion of the outer surface of the sheath 210. In some embodiments, the sleeve or cover may be formed or a bioabsorbable material.

As illustrated in FIG. 8, the implant may be placed or disposed within a penis P of a patient or user. In the illustrated embodiment, a first implant 200A and a second implant 200B are disposed or placed within the penis of the patient. The implants are placed in a parallel or side-by-side relationship (with the urethra of the patient extending between the implants). In some embodiments, only one implant is disposed within the patient. Additionally, in some embodiments, the implant is placed or disposed in another portion of the body of the patient.

In use, a user or patient may straighten their penis to place the implant 200 in its first, straight, or linear configuration. For example, a user may grasp and lift an end of their penis to straighten their penis and place the implant 200 in its first, straight, or linear configuration (for example, as illustrated in FIG. 5). The lifting and end portion or straightening of the implant 200 will cause the plunger member 252 to move towards the first end portion 218 of the sheath 210 (against the bias of the bias member 254). The release members 258 and 260 will engage the plunger member 252 to retain the plunger member 252 in place. This movement will apply tension to the sheath 210 via the cable 230. In this configuration, the sheath 210 is retained in its first, straight, or linear configuration.

A user or patient may activate or press on the release members 258 and 260 to release the tension applied to the sheath 210 and allow the sheath to assume its second, curved, or non-linear configuration. As best illustrated in FIG. 6, when the release members 258 and 260 are moved or activated by a user, the retention member is moved out of engagement with the plunger 252 and the bias member 254 moves the plunger towards the second end portion 220 of the sheath 210. This movement removes the tension on the sheath 210 and allows the sheath to assume its second, curved, or non-linear configuration.

In some embodiments, the implant 200 is configured such that a sufficient force on the sheath 210 (for example, a force that would place the sheath 210 in a curved configuration), will cause the release members 258 and 260 to disengage the plunger member 252 and allow the sheath 210 to assume its second, curved, or non-linear configuration.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical implant, comprising:
a sheath defining a lumen, a first window and a second window, the sheath being configured to be placed in a first tensioned configuration and second non-tensioned configuration; and a tensioner having a first release member and a second release member, the first release member and the second release member each being moveable between a tension retention position, wherein tension is retained in the sheath, and a tension release position, wherein tension is released from the sheath,
wherein the first release member is accessible and operable through the first window defined by the sheath and the second release member is accessible and operable through the second window defined by the sheath, whereby a portion of the first release member is configured to extend through the first window defined by the sheath and a portion of the second release member is configured to extend through the second window defined by the sheath.

2. The implant according to claim 1, wherein in the first tensioned configuration, the sheath has a linear configuration and in the second non-tensioned configuration, the sheath has a curved configuration.

3. The implant according to claim 1, further comprising a bias member, wherein the bias member provides a bias to the tensioner such that tension is removed from the sheath, and the sheath assumes the second, non-tensioned configuration, preferably wherein the bias member is a spring element.

4. The implant according to claim 1, wherein the first release member is pivotably movable between the tension retention position and the release positions, with respect to the sheath.

5. The implant according to claim 1, wherein the tensioner includes a plunger member and a plunger guide separated by the bias member, wherein a cable member extends through the plunger member, a bias member and a plunger guide.

6. The implant according to claim 5, wherein in the first tensioned configuration of the sheath, an engagement portion of the first release member engages a plunger member.

7. The implant according to claim 6, wherein in the second non-tensioned configuration of the sheath, the engagement portion of the first release member is disengaged from the plunger member.

8. The implant according to claim 5, wherein the first release member includes an activation portion, for moving the release member for disengaging the plunger member from the engagement portion of the first release member, whereby the plunger member is movable by the bias member so that the sheath assumes the second configuration.

9. The implant according to claim 1, wherein the sheath defines a plurality of slots arranged at slot locations in a sidewall of the sheath, which slots facilitate flexibility of the sheath, wherein the slots are configured to engage each other and lock into place such that columnar strength of the sheath is increased when the sheath is in the first tensioned configuration.

10. An implant comprising:
a sheath defining a lumen and an opening;
a cable member having a first portion coupled to the sheath at a first location and a second end portion coupled to the sheath at a second location, the cable member being disposed within the lumen of the sheath; and
a tensioner configured to engage the cable to apply tension to the sheath, the tensioner includes a release member, the release member being configured to accessible through the opening defined by the sheath.

11. The implant of claim 10, wherein the sheath is configured to be placed in a linear configuration and a curved configuration.

12. The implant of claim 10, wherein the cable member has a first end portion and second end portion, the first end portion of the cable member being operatively coupled within the lumen defined by the sheath, the second end portion of the cable member being operatively coupled within the lumen defined by the sheath.

13. The implant of claim 10, wherein the cable member has a first end portion and second end portion, the first end portion of the cable member being operatively coupled at a first end portion of the lumen defined by the sheath, the second end portion of the cable member being operatively coupled at a second end portion of the lumen defined by the sheath.

14. The implant of claim 10, wherein the tensioner includes a bias member.

15. The implant of claim 10, wherein the release member is configured to extend through the opening defined by the sheath.

16. The implant of claim 10, wherein the release member is movable with respect to the sheath.

17. The implant of claim 10, wherein the tensioner includes a plunger member, the release member is configured to engage the plunger member to help retain the sheath in a linear configuration.

18. The implant of claim 10, wherein the tensioner includes a second release member.

19. The implant of claim 10, wherein the sheath defines a plurality of slots.

* * * * *